United States Patent [19]
Reinscheid et al.

[11] Patent Number: 5,965,391
[45] Date of Patent: Oct. 12, 1999

[54] DNA WHICH REGULATES GENE EXPRESSION IN CORYNEFORM BACTERIA

[75] Inventors: Dieter Reinscheid, Braunschweig; Bernhard Eikmanns; Hermann Sahm, both of Jülich, all of Germany

[73] Assignee: Forschungszentrum Julich GmbH, Julich, Germany

[21] Appl. No.: 08/836,943

[22] PCT Filed: Nov. 7, 1995

[86] PCT No.: PCT/DE95/01555

§ 371 Date: May 8, 1997

§ 102(e) Date: May 8, 1997

[87] PCT Pub. No.: WO96/15246

PCT Pub. Date: May 23, 1996

[30] Foreign Application Priority Data

Nov. 11, 1994 [DE] Germany .................. 44 40 118

[51] Int. Cl.$^6$ .............. C12P 21/00; C12N 1/21; C12N 15/77; C07H 21/04

[52] U.S. Cl. .............. 435/69.1; 435/252.32; 435/320.1; 435/471; 435/476; 435/487; 536/24.1

[58] Field of Search ............... 435/69.1, 172.1, 435/172.3, 320.1, 252.3, 252.32, 487, 471, 476; 536/23.1, 23.7, 24.1

[56] References Cited

FOREIGN PATENT DOCUMENTS 0 530 765 A2  3/1993  European Pat. Off. .

OTHER PUBLICATIONS

Biochemical Journal, 99 (1966), pp. 1–11, Kornberg, H.L.
Biology of Industrial Microorganisms, 1985, pp. 115 to 142, Kinoshita, S.
Applied and Environmental Microbiology, 60, (1994), pp. 126 to 132, Reinscheid et al.
Microbiology, 140 (1994), 1817 to 1828, Eikmanns et al.
Bio/Technology 6 (1988) pp. 428 to 431, Tsuchiya et al.
"Malate synthase from C. glutamicum: sequence analysis of the gene and biochmical characterization of the enzyme" by Reinscheid et al., published in Microbiology, vol. 140, 1994.

*Primary Examiner*—David Guzo
*Attorney, Agent, or Firm*—Herbert Dubno; Jonathan Myers

[57] ABSTRACT

The invention concerns a DNA fragment located in front of the malate synthase gene of a coryne-form bacterium and isolated from the latter. Any structural gene which codes for a protein can be inserted after this DNA fragment. After transformation of such a construct into a coryne-form bacterium, expression of the structural gene inserted after the DNA fragment is regulated. The invention also concerns a process for synthesizing any protein by culturing a transformed coryne-form bacterium. A bacterium of this type contains in replicable form a DNA fragment isolated from the malate synthase gene of a coryne-form bacterium, and after which the structural gene which codes for the protein to be synthesized is inserted. Since expression of the structural gene which codes for the protein to be synthesized is regulated by the DNA located in front of it, the structural gene is expressed and the desired protein synthesized as soon as a suitable inducing agent is added to the medium.

10 Claims, 4 Drawing Sheets

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
(A) LENGTH: 3024 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Corynebacterium glutamicum
(B) STRAIN: ATCC 13032

(ix) FEATURE:
(A) NAME/KEY: CDS
(B) LOCATION: 586..2805

(xi) SEQUENCE DESCRIPTION: SEQ ID NO:1:

```
CTTAAGTGCT GATTCGCAAT GGGCGGTGCC GACCACAAAG TATGAGCTAA TGCACTGTCA      60

CTGTTTCGAC GTGATGTGCA TCGGTTTGCG TGGTGGCGTG GTTCACACAT TGCTCCATCG     120

GGCATTGGTG CGTCAATCGG TTTGGGTTTT TAAGTTTTGT GCGGGGTGG TCACCCCTGT      180

TGTGAAGTTT GCAAAGTTCT GGCTTCGCAG AAAAAGTGGG CGGGGGAGTT GCTAGTACGG     240

ATGTACTGGG CAAATGCTCT GAAATGGGAA AATGCAGGCA CCGCAACGTT CCGTAGGTTT     300

CGAAGGTGTG ACCTAGATAA AAGTCGGGGT TAGGCGGGGG TAATGACTTA GTAAAGTTCG     360

CAAACCCCTT TTGCTGGTGA CGGTGATCAC TTAGTCTGAT CACATCGCCA AACACGATAA     420

GGGTTGAAAT CGAAAGAAGA GTGGCACCTA GATTCCAGAG GTAGTCAGAG TGCTTTTCTT     480

AAAAGAGTTT TCACAACCGT TAACGCGTAG CCAAACAAGA AGGATTCGCA TTCTTCTGGT     540

TTAGGCACAG GTCATCTAAA ACCCATGCTT TAAAAGGAGC CTTCA ATG ACT GAA         594
                                                  Met Thr Glu
                                                   1
```

```
CAG GAA CTG TTG TCT GCT CAG ACT GCC GAC AAC GCT GGA ACT GAC AGC      642
Gln Glu Leu Leu Ser Ala Gln Thr Ala Asp Asn Ala Gly Thr Asp Ser
      5                  10                  15

ACC GAA CGC GTT GAC GCG GGC GGA ATG CAG GTT GCA AAA GTT CTC TAC      690
Thr Glu Arg Val Asp Ala Gly Gly Met Gln Val Ala Lys Val Leu Tyr
 20                  25                  30                  35

GAC TTT GTA ACC GAA GCG GTA CTC CCT CGC GTG GGT GTG GAT GCG GAA      738
Asp Phe Val Thr Glu Ala Val Leu Pro Arg Val Gly Val Asp Ala Glu
                 40                  45                  50

AAG TTC TGG TCC GGA TTC GCC GCC ATC GCC CGG GAC CTC ACC CCA CGC      786
Lys Phe Trp Ser Gly Phe Ala Ala Ile Ala Arg Asp Leu Thr Pro Arg
             55                  60                  65

AAC CGC GAG CTG CTT GCT CGC CGC GAT GAA CTG CAG ATG CTT ATC GAC      834
Asn Arg Glu Leu Leu Ala Arg Arg Asp Glu Leu Gln Met Leu Ile Asp
         70                  75                  80

GAC TAC CAC CGC AAC AAC TCC GGC ACC ATC GAC CAA GAG GCG TAC GAG      882
Asp Tyr His Arg Asn Asn Ser Gly Thr Ile Asp Gln Glu Ala Tyr Glu
     85                  90                  95
```

-continued

| | |
|---|---|
| GAT TTC CTC AAA GAA ATC GGA TAC TTG GTT GAG GAG CCA GAA GCT GCA<br>Asp Phe Leu Lys Glu Ile Gly Tyr Leu Val Glu Glu Pro Glu Ala Ala<br>100                        105                        110                        115 | 930 |
| GAA ATC CGT ACC CAA AAC GTC GAT ACG GAA ATC TCC AGC ACC GCA GGA<br>Glu Ile Arg Thr Gln Asn Val Asp Thr Glu Ile Ser Ser Thr Ala Gly<br>                    120                        125                        130 | 978 |
| CCT CAG CTG GTT GTT CCA ATT CTG AAC GCA CGC TTC GCG CTG AAC GCT<br>Pro Gln Leu Val Val Pro Ile Leu Asn Ala Arg Phe Ala Leu Asn Ala<br>               135                        140                        145 | 1026 |
| GCC AAT GCT CGC TGG GGT TCC CTC TAC GAT GCG TTG TAC GGC ACC AAC<br>Ala Asn Ala Arg Trp Gly Ser Leu Tyr Asp Ala Leu Tyr Gly Thr Asn<br>          150                        155                        160 | 1074 |
| GCC ATC CCA GAA ACT GAT GGC GCT GAA AAG GGC AAG GAG TAC AAC CCG<br>Ala Ile Pro Glu Thr Asp Gly Ala Glu Lys Gly Lys Glu Tyr Asn Pro<br>165                        170                        175 | 1122 |
| GTC CGC GGC CAG AAG GTC ATC GAG TGG GGT CGT GAA TTC CTC GAC AGC<br>Val Arg Gly Gln Lys Val Ile Glu Trp Gly Arg Glu Phe Leu Asp Ser<br>180                        185                        190                        195 | 1170 |
| GTT GTC CCA CTG GAC GGT GCT TCG CAT GCC GAT GTT GAG AAG TAC AAC<br>Val Val Pro Leu Asp Gly Ala Ser His Ala Asp Val Glu Lys Tyr Asn<br>                    200                        205                        210 | 1218 |
| ATC ACC GAT GGA AAG CTT GCA GCC CAC ATT GGA GAT AGC GTC TAC CGA<br>Ile Thr Asp Gly Lys Leu Ala Ala His Ile Gly Asp Ser Val Tyr Arg<br>               215                        220                        225 | 1266 |
| CTG AAA AAC CGT GAA TCC TAC CGT GGC TTC ACC GGC AAC TTC CTT GAT<br>Leu Lys Asn Arg Glu Ser Tyr Arg Gly Phe Thr Gly Asn Phe Leu Asp<br>          230                        235                        240 | 1314 |
| CCA GAA GCA ATC CTG CTG GAA ACC AAC GGC CTG CAC ATC GAG CTG CAG<br>Pro Glu Ala Ile Leu Leu Glu Thr Asn Gly Leu His Ile Glu Leu Gln<br>245                        250                        255 | 1362 |
| ATC GAT CCT GTC CAC CCA ATC GGC AAG GCA GAC AAG ACT GGT CTC AAA<br>Ile Asp Pro Val His Pro Ile Gly Lys Ala Asp Lys Thr Gly Leu Lys<br>260                        265                        270                        275 | 1410 |
| GAC ATC GTT TTG GAA TCT GCG ATC ACC ACG ATC ATG GAC TTC GAA GAC<br>Asp Ile Val Leu Glu Ser Ala Ile Thr Thr Ile Met Asp Phe Glu Asp<br>                    280                        285                        290 | 1458 |
| TCC GTT GCA GCT GTT GAT GCT GAA GAC AAG ACC TTA GGT TAC TCT AAC<br>Ser Val Ala Ala Val Asp Ala Glu Asp Lys Thr Leu Gly Tyr Ser Asn<br>               295                        300                        305 | 1506 |
| TGG TTC GGA CTC AAC ACC GGC GAA CTG AAA GAA GAG ATG TCC AAG AAC<br>Trp Phe Gly Leu Asn Thr Gly Glu Leu Lys Glu Glu Met Ser Lys Asn<br>          310                        315                        320 | 1554 |
| GGA CGC ATC TTC ACC CGT GAG CTC AAC AAG GAC CGC GTC TAC ATT GGC<br>Gly Arg Ile Phe Thr Arg Glu Leu Asn Lys Asp Arg Val Tyr Ile Gly<br>325                        330                        335 | 1602 |
| CGC AAT GGT ACC GAG CTG GTT CTG CAC GGT CGT TCC CTG CTG TTC GTC<br>Arg Asn Gly Thr Glu Leu Val Leu His Gly Arg Ser Leu Leu Phe Val<br>340                        345                        350                        355 | 1650 |
| CGC AAC GTT GGT CAC CTC ATG CAA AAC CCA TCC ATC TTG ATT GAT GGC<br>Arg Asn Val Gly His Leu Met Gln Asn Pro Ser Ile Leu Ile Asp Gly<br>               360                        365                        370 | 1698 |
| GAG GAG ATC TTC GAA GGC ATC ATG GAT GCT GTC TTG ACC ACT GTT TGT<br>Glu Glu Ile Phe Glu Gly Ile Met Asp Ala Val Leu Thr Thr Val Cys<br>          375                        380                        385 | 1746 |
| GCC ATC CCA GGA ATT GCT CCG CAG AAC AAG ATG CGC AAT TCC CGC AAG<br>Ala Ile Pro Gly Ile Ala Pro Gln Asn Lys Met Arg Asn Ser Arg Lys<br>390                        395                        400 | 1794 |
| GGC TCC ATC TAC ATC GTG AAG CCT AAG CAG CAC GGC CCT GAA GAA GTC<br>Gly Ser Ile Tyr Ile Val Lys Pro Lys Gln His Gly Pro Glu Glu Val<br>405                        410                        415 | 1842 |

-continued

| | |
|---|---|
| GCG TTC ACC AAC GAG CTC TTC GGC CGC GTT GAG GAT CTG CTT GAT CTG<br>Ala Phe Thr Asn Glu Leu Phe Gly Arg Val Glu Asp Leu Leu Asp Leu<br>420                        425                    430                    435 | 1890 |
| CCA CGC CAC ACC TTG AAG GTT GGT GTT ATG GAT GAG GAG CGT CGC ACG<br>Pro Arg His Thr Leu Lys Val Gly Val Met Asp Glu Glu Arg Arg Thr<br>                    440                    445                    450 | 1938 |
| TCC GTG AAC CTG GAT GCC AGC ATC ATG GAA GTT GCT GAC CGC TTG GCA<br>Ser Val Asn Leu Asp Ala Ser Ile Met Glu Val Ala Asp Arg Leu Ala<br>                    455                    460                    465 | 1986 |
| TTC ATC AAC ACT GGC TTC CTG GAC CGC ACC GGC GAT GAA ATC CAC ACC<br>Phe Ile Asn Thr Gly Phe Leu Asp Arg Thr Gly Asp Glu Ile His Thr<br>                    470                    475                    480 | 2034 |
| TCC ATG GAA GCA GGC GCC ATG GTG CGC AAG GCT GAT ATG CAG ACC GCA<br>Ser Met Glu Ala Gly Ala Met Val Arg Lys Ala Asp Met Gln Thr Ala<br>485                        490                    495 | 2082 |
| CCG TGG AAG CAG GCC TAC GAG AAC AAC AAC GTT GAT GCA GGT ATT CAG<br>Pro Trp Lys Gln Ala Tyr Glu Asn Asn Asn Val Asp Ala Gly Ile Gln<br>500                        505                    510                    515 | 2130 |
| CGT GGT CTT CCT GGC AAG GCT CAG ATC GGT AAG GGC ATG TGG GCG ATG<br>Arg Gly Leu Pro Gly Lys Ala Gln Ile Gly Lys Gly Met Trp Ala Met<br>                    520                    525                    530 | 2178 |
| ACT GAA CTC ATG GCA GAA ATG CTG GAG AAG AAG ATC GGC CAG CCA CGC<br>Thr Glu Leu Met Ala Glu Met Leu Glu Lys Lys Ile Gly Gln Pro Arg<br>                    535                    540                    545 | 2226 |
| GAA GGC GCC AAC ACT GCA TGG GTT CCT TCA CCA ACT GGT GCG ACG CTG<br>Glu Gly Ala Asn Thr Ala Trp Val Pro Ser Pro Thr Gly Ala Thr Leu<br>                550                    555                    560 | 2274 |
| CAC GCA ACG CAC TAC CAC TTG GTT GAT GTG TTC AAG GTT CAA GAC GAA<br>His Ala Thr His Tyr His Leu Val Asp Val Phe Lys Val Gln Asp Glu<br>                    565                    570                    575 | 2322 |
| CTG CGT GCT GCC GGC CGC CGC GAC AGC CTG CGC AAC ATT CTC ACC ATT<br>Leu Arg Ala Ala Gly Arg Arg Asp Ser Leu Arg Asn Ile Leu Thr Ile<br>580                        585                    590                    595 | 2370 |
| CCA ACC GCA CCA AAC ACC AAT TGG TCT GAG GAA GAG AAG AAG GAA GAG<br>Pro Thr Ala Pro Asn Thr Asn Trp Ser Glu Glu Glu Lys Lys Glu Glu<br>                    600                    605                    610 | 2418 |
| ATG GAC AAC AAC TGC CAG TCC ATC CTC GGA TAC GTT GTG CGC TGG GTT<br>Met Asp Asn Asn Cys Gln Ser Ile Leu Gly Tyr Val Val Arg Trp Val<br>                    615                    620                    625 | 2466 |
| GAG CAC GGT GTT GGT TGC TCC AAG GTT CCA GAC ATC CAT GAC ATC GAC<br>Glu His Gly Val Gly Cys Ser Lys Val Pro Asp Ile His Asp Ile Asp<br>                630                    635                    640 | 2514 |
| CTC ATG GAA GAC CGC GCA ACG CTG CGT ATT TCC TCG CAG ATG CTG GCC<br>Leu Met Glu Asp Arg Ala Thr Leu Arg Ile Ser Ser Gln Met Leu Ala<br>              645                    650                    655 | 2562 |
| AAC TGG ATC CGC CAT GAT GTT GTC TCG AAG GAG CAG GTC TTG GAG TCA<br>Asn Trp Ile Arg His Asp Val Val Ser Lys Glu Gln Val Leu Glu Ser<br>660                        665                    670                    675 | 2610 |
| CTG GAA CGA ATG GCA GTG GTC GTC GAC AAG CAA AAT GCG GGC GAC GAG<br>Leu Glu Arg Met Ala Val Val Val Asp Lys Gln Asn Ala Gly Asp Glu<br>                    680                    685                    690 | 2658 |
| GCC TAC CGC GAT ATG GCG CCG AAC TAC GAC GCC TCC CTC GCC TTC CAG<br>Ala Tyr Arg Asp Met Ala Pro Asn Tyr Asp Ala Ser Leu Ala Phe Gln<br>                  695                    700                    705 | 2706 |
| GCG GCT AAG GAC TTG ATT TTC GAA GGC ACC AAG TCC CCA TCG GGC TAC<br>Ala Ala Lys Asp Leu Ile Phe Glu Gly Thr Lys Ser Pro Ser Gly Tyr<br>            710                    715                    720 | 2754 |
| ACC GAG CCC ATC TTG CAC GCA CGC CGC CGC GAG TTC AAA GCA AAA AAC<br>Thr Glu Pro Ile Leu His Ala Arg Arg Arg Glu Phe Lys Ala Lys Asn<br>725                        730                    735 | 2802 |

-continued

```
TAA GCACGCTTTT CGACGCTTAC CTGCATCCCA ACGGTGACTG ACTGCCCCGG        2855
 *
740

AGCCACCCTC ACTCCTTTTT GGTCAGCACC CAAAAGCGCC GGTTCAACAC ACACAAAGTC  2915

GCGCCATTCA CCTTCGCCAA TATCGGCCAC GGTGGAGGCG CGACTTTCGC CTGGATTCCA  2975

CACCACAGTG GAATCATGAC CATCGCCCTC AATGGTGATG ATGCGATCG             3024
```

(2) INFORMATION FOR SEQ ID NO:2:

(i) SEQUENCE CHARACTERISTICS:
        (A) LENGTH: 739 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Thr Glu Gln Glu Leu Leu Ser Ala Gln Thr Ala Asp Asn Ala Gly
 1               5                  10                  15

Thr Asp Ser Thr Glu Arg Val Asp Ala Gly Gly Met Gln Val Ala Lys
             20                  25                  30

Val Leu Tyr Asp Phe Val Thr Glu Ala Val Leu Pro Arg Val Gly Val
         35                  40                  45

Asp Ala Glu Lys Phe Trp Ser Gly Phe Ala Ala Ile Ala Arg Asp Leu
     50                  55                  60

Thr Pro Arg Asn Arg Glu Leu Leu Ala Arg Arg Asp Glu Leu Gln Met
 65                  70                  75                  80

Leu Ile Asp Asp Tyr His Arg Asn Asn Ser Gly Thr Ile Asp Gln Glu
                 85                  90                  95

Ala Tyr Glu Asp Phe Leu Lys Glu Ile Gly Tyr Leu Val Glu Glu Pro
            100                 105                 110

Glu Ala Ala Glu Ile Arg Thr Gln Asn Val Asp Thr Glu Ile Ser Ser
        115                 120                 125

Thr Ala Gly Pro Gln Leu Val Val Pro Ile Leu Asn Ala Arg Phe Ala
    130                 135                 140

Leu Asn Ala Ala Asn Ala Arg Trp Gly Ser Leu Tyr Asp Ala Leu Tyr
145                 150                 155                 160

Gly Thr Asn Ala Ile Pro Glu Thr Asp Gly Ala Glu Lys Gly Lys Glu
                165                 170                 175

Tyr Asn Pro Val Arg Gly Gln Lys Val Ile Glu Trp Gly Arg Glu Phe
            180                 185                 190

Leu Asp Ser Val Val Pro Leu Asp Gly Ala Ser His Ala Asp Val Glu
        195                 200                 205

Lys Tyr Asn Ile Thr Asp Gly Lys Leu Ala Ala His Ile Gly Asp Ser
    210                 215                 220

Val Tyr Arg Leu Lys Asn Arg Glu Ser Tyr Arg Gly Phe Thr Gly Asn
225                 230                 235                 240

Phe Leu Asp Pro Glu Ala Ile Leu Leu Glu Thr Asn Gly Leu His Ile
                245                 250                 255

Glu Leu Gln Ile Asp Pro Val His Pro Ile Gly Lys Ala Asp Lys Thr
            260                 265                 270

Gly Leu Lys Asp Ile Val Leu Glu Ser Ala Ile Thr Thr Ile Met Asp
        275                 280                 285

Phe Glu Asp Ser Val Ala Ala Val Asp Ala Glu Asp Lys Thr Leu Gly
    290                 295                 300
```

-continued

```
Tyr Ser Asn Trp Phe Gly Leu Asn Thr Gly Glu Leu Lys Glu Met
305                 310                 315                 320

Ser Lys Asn Gly Arg Ile Phe Thr Arg Glu Leu Asn Lys Asp Arg Val
            325                 330                 335

Tyr Ile Gly Arg Asn Gly Thr Glu Leu Val Leu His Gly Arg Ser Leu
            340                 345                 350

Leu Phe Val Arg Asn Val Gly His Leu Met Gln Asn Pro Ser Ile Leu
        355                 360                 365

Ile Asp Gly Glu Glu Ile Phe Glu Gly Ile Met Asp Ala Val Leu Thr
    370                 375                 380

Thr Val Cys Ala Ile Pro Gly Ile Ala Pro Gln Asn Lys Met Arg Asn
385                 390                 395                 400

Ser Arg Lys Gly Ser Ile Tyr Ile Val Lys Pro Lys Gln His Gly Pro
            405                 410                 415

Glu Glu Val Ala Phe Thr Asn Glu Leu Phe Gly Arg Val Glu Asp Leu
            420                 425                 430

Leu Asp Leu Pro Arg His Thr Leu Lys Val Gly Val Met Asp Glu Glu
        435                 440                 445

Arg Arg Thr Ser Val Asn Leu Asp Ala Ser Ile Met Glu Val Ala Asp
    450                 455                 460

Arg Leu Ala Phe Ile Asn Thr Gly Phe Leu Asp Arg Thr Gly Asp Glu
465                 470                 475                 480

Ile His Thr Ser Met Glu Ala Gly Ala Met Val Arg Lys Ala Asp Met
            485                 490                 495

Gln Thr Ala Pro Trp Lys Gln Ala Tyr Glu Asn Asn Asn Val Asp Ala
            500                 505                 510

Gly Ile Gln Arg Gly Leu Pro Gly Lys Ala Gln Ile Gly Lys Gly Met
        515                 520                 525

Trp Ala Met Thr Glu Leu Met Ala Glu Met Leu Glu Lys Lys Ile Gly
    530                 535                 540

Gln Pro Arg Glu Gly Ala Asn Thr Ala Trp Val Pro Ser Pro Thr Gly
545                 550                 555                 560

Ala Thr Leu His Ala Thr His Tyr His Leu Val Asp Val Phe Lys Val
            565                 570                 575

Gln Asp Glu Leu Arg Ala Ala Gly Arg Arg Asp Ser Leu Arg Asn Ile
            580                 585                 590

Leu Thr Ile Pro Thr Ala Pro Asn Thr Asn Trp Ser Glu Glu Glu Lys
        595                 600                 605

Lys Glu Glu Met Asp Asn Asn Cys Gln Ser Ile Leu Gly Tyr Val Val
    610                 615                 620

Arg Trp Val Glu His Gly Val Gly Cys Ser Lys Val Pro Asp Ile His
625                 630                 635                 640

Asp Ile Asp Leu Met Glu Asp Arg Ala Thr Leu Arg Ile Ser Ser Gln
            645                 650                 655

Met Leu Ala Asn Trp Ile Arg His Asp Val Val Ser Lys Glu Gln Val
            660                 665                 670

Leu Glu Ser Leu Glu Arg Met Ala Val Val Asp Lys Gln Asn Ala
        675                 680                 685

Gly Asp Glu Ala Tyr Arg Asp Met Ala Pro Asn Tyr Asp Ala Ser Leu
    690                 695                 700

Ala Phe Gln Ala Ala Lys Asp Leu Ile Phe Glu Gly Thr Lys Ser Pro
705                 710                 715                 720

Ser Gly Tyr Thr Glu Pro Ile Leu His Ala Arg Arg Glu Phe Lys
            725                 730                 735
```

```
Ala Lys Asn
           740

(2) INFORMATION FOR SEQ ID NO:3:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Corynebacterium glutamicum
        (B) STRAIN: ATCC 13032

(xi) SEQUENCE DESCRIPTION: SEQ ID NO:3:

CTTAAGTGCT GATTCGCAAT GGGCGGTGCC GACCACAAAG TATGAGCTAA TGCACTGTCA        60

CTGTTTCGAC GTGATGTGCA TCGGTTTGCG TGGTGGCGTG GTTCACACAT TGCTCCATCG       120

GGCATTGGTG CGTCAATCGG TTTGGGTTTT TAAGTTTTGT GCGGGGGTGG TCACCCCTGT       180

TGTGAAGTTT GCAAAGTTCT GGCTTCGCAG AAAAAGTGGG CGGGGGAGTT GCTAGTACGG       240

ATGTACTGGG CAAATGCTCT GAAATGGGAA AATGCAGGCA CCGCAACGTT CCGTAGGTTT       300

CGAAGGTGTG ACCTAGATAA AAGTCGGGGT TAGGCGGGGG TAATGACTTA GTAAAGTTCG       360

CAAACCCCTT TTGCTGGTGA CGGTGATCAC TTAGTCTGAT CACATCGCCA AACACGATAA       420

GGGTTGAAAT CGAAAGAAGA GTGGCACCTA GATTCCAGAG GTAGTCAGAG TGCTTTTCTT       480

AAAAGAGTTT TCACAACCGT TAACGCGTAG CCAAACAAGA AGGATTCGCA TTCTTCTGGT       540

TTAGGCACAG GTCATCTAAA ACCCATGCTT TAAA                                   574
```

DNA WHICH REGULATES GENE EXPRESSION IN CORYNEFORM BACTERIA

This application is a 371 application of PCT/DE95/01555, filed Nov. 7, 1995.

FIELD OF THE INVENTION

The invention relates to a DNA which regulates gene expression in coryneform bacteria.

BACKGROUND OF THE INVENTION

Each organism is required, in the course of growth to synthesize new cell substances. There are numerous cell components, like, for example, amino acids and porphyrins which are to be newly formed starting from metabolites of the citrate cycle. This means that the metabolites involved in the citrate cycle must be newly synthesized. In the growth of microorganisms on acetate, ethanol or fatty acids, metabolites of the acetate cycle are newly synthesized by a reaction sequence which has been called the glyoxylate cycle (Kornberg, Biochemical Journal 99 (1966) 1–11), key enzymes for the glyoxylate cycle being the enzymes isocitrate lyase and malate synthase. Since the named enzymes in many organisms can grow exclusively on acetate, ethanol or fatty acids, but not on carbohydrates, the activity or the new synthesis of the two enzymes is mainly regulated by the carbon source of the medium.

Because of their club-like configuration, *Corynebacterium glutamicum* and the closely associated *C. melassocolae, B. flavum* and *B. lactofermentum* are counted as coryneform bacteria. These types of bacteria also belong to the known class of "glutamic acid bacteria" since they are capable under certain growth conditions of liberating large amounts of glutamate in the medium. The named microorganisms are of considerable industrial interest since they can be used for the production of amino acids, purines and proteins. For *C. glutamicum, C. melassecolae, B. flavum* and *B. lactofermentum*, growth upon acetate or ethanol is already known and it has been found that they are involved in a glyoxylate cycle, i.e. also utilize the enzymes isocitrate lyase and malate synthase (for an overview see Kinoshita, Amino acids, in Biology of Industrial Organisms, 1985, pages 115–142, Benjamin/Cummings Publishing).

In spite of long term industrial use of these organisms only recently have molecular biological methods been developed with the aid of which coryneform bacteria can be genetically modified for certain specific purposes. As a rule, the gene to be cloned is cloned under the control of its own promoters on vectors which are available in higher copy numbers in coryneform bacteria. It has been found in many cases that a strong overexpression of individual genes is a drawback to the growth of coryneform bacteria and thus has an effect on the production of desired products. This has its origin in an overproduction of the corresponding gene products to toxic effects within the metabolism of the cell and gives rise to a reduction in the growth of these cell. An example of such a case is the homologous overexpression of mutated genes which code for deregulated enzymes, i.e. such enzymes whose activity no longer has end product blocking, for instance, the homologous overexpression of the HOM 1 gene which codes for a deregulated homoserine dehydrogenase (Reinscheid et al., Applied the Environmental Microbiology 60 (1994), 126–132). There are however, also known cases in which the overexpression of nonmutated genes is detrimental in a homologous system for the growth of *C. glutamicum* (for example Eikmanns et al., Microbiology 140 (1994) 1817–1828). In addition, there are significant problems when genes, which do not stem from coryneform bacteria, should be overexpressed in them. In order to express a desired gene in coryneform bacteria, without having to take into consideration a growth blockage by the corresponding gene product, there are various possibilities: a desired gene can be integrated in a single copy number in the chromosome of coryneform bacteria. Since one copy of these genes is provided in the organism, as a rule, no toxic effects arise from the corresponding gene product. A weakness of this process is found in the work-intensive methodology to achieve the desired goal. In addition, with a single copy number of the inserted gene, seldom is a sufficient quantity of a desired material formed.

An alternative to the integration of a gene in the chromosome of coryneform bacteria is the cloning of a gene on a vector with low copy number in coryneform bacteria. This has the advantage that the corresponding gene product is formed in relatively small amounts and thus usually is not toxic for the cells. However, also in this case a relatively small quantity of the gene product is formed which for biotechnological purposes is a drawback.

It has been desired to form a certain gene product in a large quantity only to a certain point in time in order to overcome the disadvantageous effects of this gene product on the production or growth of the microorganism. To achieve this goal the tendency has been to clone a desired gene without its own promoter behind a controllable promoter. For the controllable *Escherichia coli* promoters lac, Lambda $P_L$ and trp have already been indicated for use in coryneform bacteria to regulate expression of various genes (Tsuchiya and Morinaga, Bio/Technology 6 (1988) 428–431). However, these promoters have various drawbacks; these promoters do not stem from coryneform organisms and thus have foreign DNA. By the incorporation of such a promoter in coryneform bacteria, these become recombinant organisms for which stricter safety rules apply. In addition, the conditions which are necessary for each of the three promoters for induction of a gene are relatively uninteresting for industrial purposes. Thus the lac-promoter, for induction of a gene, requires the relatively expensive substance IPTG which makes the large-scale use of this promoter uneconomical. The promoter Lambda $P_L$ is activated by heat. Heat, however, not only damages the organisms but also has a detrimental effect to the product formed so that this promoter has no industrial interest for coryneform bacteria. The trp-promoter is activated by a tryptophan deficiency. As a rule coryneform bacteria does not suffer from tryptophan deficiency so that the use of this promoter is preconditioned on the production of coryneform tryptophan deficient mutants. Since the recovery of such mutants is relatively expensive, even the trp-promoter has not found up to now any involvement in the biotechnological use with coryneform bacteria.

The ideal case for a controllable promoter is a coryneform promoter which can be regulated by an easily available inexpensive substance. The hitherto single coryneform promotor described is that of the gene for isocitrate lyase (EP-OS 0 530 765). This promotor leads to expression of genes as long as no sugar is present in the medium. Since sugar is introduced as a carbon source in most fermentation mediums it is sensible to obtain a controllable promoter which also gives rise to expression of a gene in the presence of sugar with an inexpensive inductor.

OBJECT OF THE INVENTION

It is thus the object of the invention to provide a DNA fragment which enables, independently of the carbon source of the culture medium, a controlled expression of different genes in coryneform bacteria.

SUMMARY OF THE INVENTION

This object is achieved according to the invention with a DNA fragment which precedes the malate synthase gene of a coryneform bacteria and which is isolated therefrom and which can express an optional structure gene coding for a protein after incorporation behind the DNA fragment in a vector and regulates transformation in a coryneform bacteria.

It can be determined that the expression of the malate synthase gene in coryneform bacteria is induced by the presence of inductors as for example lactate, pyruvate, and/or acetate. This induction is especially effected by acetate even when still other carbon sources are present in the medium. Thus even in the presence of sugars or in complex media, a significant induction is effected by acetate.

After isolation of a DNA fragment preceding the malate synthase gene of a coryneform bacteria, the optional structure gene is connected to it which codes for a protein to be synthesized, this construct being ligated into a vector and then transformed in a coryneform bacterium. During the cultivation of such a transformant, at an optional point in time, the inductor, like lactate, pyruvate and preferably acetate, is added to the medium whereupon the structure gene is expressed at the desired point in time and thus the desired protein is synthesized. The DNA fragment prepared according to the invention thus enables the controlled expression of various genes in coryneform bacteria. Since the isolated DNA itself stems from a coryneform bacterium, the above described regulation occurs within a homologous system. The DNA regions according to the invention permit for the first time the possibility of regulated expression of genes in coryneform bacteria in a homologous system using an inexpensive indicator like acetate and independent of the composition of the fermentation media. Advantageously the DNA fragment preceding the malate synthase gene of *Corynebacterium glutamicum* and isolated from it is prepared;

that is from *C. glutamicum* the gene for malate synthase (aceB) together with the structures necessary for expression of regulation, is isolated and sequenced. The DNA sequence and the amino acid sequence deduced therefrom is shown in Table 2. In Table 2 the ribosome binding sites of the aceB gene are underscored and indicated with "RBS". The potential terminator of the transcription of aceB is indicated by antiparallel arrows.

It can be seen that the DNA region ahead of the malate synthase gene from nucleotide 1 to nucleotide 574 according to Table 2 gives rise to controlled expression also of other genes.

BRIEF DESCRIPTION OF THE DRAWING

FIG. 3 is a restriction map of plasmid pEKB1a.

FIG. 4 is a chromatogram showing the separation by electrophoresis on 12.5% polyacrylamide gel under denaturing conditions of proteins produced by *C. glutamicum* WT cells containing plasmid pEKB1a.

EXAMPLE

1. Investigation of the Activity of Ralate Synthase in Cell Extracts of *Corynebacterium glutamicum* After Growth on Various Media.

In extracts of *C. glutamicum* strain ATCC 13032 (wild type) the activity of malate synthase (MSY) after growth of different media is determined to investigate the influence of the carbon source on the activity of this enzyme. For this purpose the cells are incubated for 14 hours in 10 ml 2xTY complete medium (Sambrook et al., Molecular Cloning, A Laboratory Handbook, 1989, Cold Spring Harbor Laboratory Press) at 30° C. with shaking (120 RPM) The cells were then sedimented by centrifugation, washed once with a buffer at pH 6.8 (0.1 M potassium phosphate) and taken up in one ml of the same buffer. Each 60 ml of medium is inoculated with the resulting cell suspension to obtain an optical density ($OD_{600}$) of 1.0. The media used were 2xTY complete medium or CgC-minimal medium (Eikmanns et al., Applied Microbiological Biotechnology 34 (1991) 617–622) with each sample containing 1% of a carbon source in the form of glucose, acetate, pyruvate, lactate, citrate, succinate, fumarate or glutamate. The cultures are again inactivated at 30° C. and, when the $OD_{600}$ reached 8 to 10, the cells were harvested by centrifugation, washed once with a buffer at pH 7.6 (50 mM Tris/HCl), taken up in 1 ml of the same buffer, and disintegrated by ultrasonic treatment in a Branson Sonifier W250 (10 minutes, pulsed with an interval of 20% and a power of 30 watts). For separation of the cell detritus, the homogenate was centrifuged for 30 minutes at 13000 RPM in a Sigma 2K15 cooled centrifuge at 4° C. and the clear supernatant (raw extract) used for determination of the MSY activity.

The enzyme test contains in its final volume of 1.0 ml, 50 mM Tris/HCl, (pH 7.6), 40 MM $MgCl_2$, 2 mM Na-Glyoxylate, 0.15 mM acetyl-coenzyme A and the raw extract. The set of samples is incubated at 30° C. Over a time period of 2 minutes, the extinction decrease at 232 nm is determined, resulting from the splitting of the thioester bond of acetyl-CoA. The extinction coefficient of acetyl-CoA at 232 nm is 4.5 $mM^{-1}$ $cm^{-1}$ (Stadtman, Methods in Enzymology, Vol. 3, 1957, New York: Academic Press). The protein content of the raw extract was determined with the aid of the Biuret Method (Bradford, Analytical Biochemistry 72 (1976) 248–254). The specific malate synthase activities are given in Table 1.

As can be seen from Table 1, the activity of MSY upon growth on 2xTY complete medium as well as on CgC minimal medium with glucose, citrate, succinate, fumarate or glutamate as the carbon sources, the MSY activity rises to a value of 0.173 U/mg protein or 0.192 U/mg protein. The highest MSY activity with 2.212 U/mg is observed in growth on CgC minimal medium with acetate. If acetate is added to the above-mentioned media, there is a strong MSY activity increase to values of 0.500 U/mg protein to 1.330 U/mg protein.

These results indicate that in *C. glutamicum* the activity of the MSY is regulatable by the carbon source in the medium.

2. Isolation and subcloning of the MSY Gene of *Corynebacterium glutamicum*.

For the isolation of the MSY gene (aceB) from *C. glutamicum*, based upon the cosmid pH 79 (Hohn and Collins, Gene 11 (1980) 291–298) a corynebacterial cosmid gene bank is achieved by a known method (Sambrook et al., Molecular Cloning, A Laboratory Handbook, 1989, Cold Spring Harbor Laboratory Press). A *C. glutamicum* chromosomal DNS is isolated and partially digested with the restriction enzyme Sau3A. After ligation of the obtained fragments in the BamHI interface of the cosmid pHC79, the composition is packed in the protein shell of the bacterial phage Lambda and the *E. coli* strain ED8654 is transferred therewith (Murray et al Molecular Gene Genetics 150 (1977) 53–61). The packing of the recombinant cosmid in the protein shell of the phage Lambda is effected according to one of the methods of Sambrook et al (Molecular Cloning, A Laboratory Handbook, 1989, Cold Spring Harbor Laboratory Press) and subjected to a restriction analysis with the enzyme HINdIII. It has been found that 24 of the investigated cosmids have inserts and that the sizes of the inserts were about 35 kb. A total of 2200 cosmid-carrying *E. Coli* clones were combined and from this mixture by known processes (Sambrook et al (Molecular Cloning, A Laboratory Handbook, 1989, Cold Spring Harbor Laboratory Press) the cosmid DNA was prepared. For isolating the aceB gene from *C. glutamicum*, the cosmid gene bank in the MSY defect *E. Coli* mutant DV21AO5 (Vanderwinkel and De Vlieghere European Journal of Biochemistry 5 (1968) 81–90) was transformed. The mutant DV21AO5 is, because of its MSY defect, no longer able to grow on acetate as the single carbon source. After transformation of the cosmid gene bank in this mutant, a total of about 1000 clones were obtained. From these, on M-9 minimal medium (Sambrook et al Molecular Cloning, A Laboratory Handbook, 1989, Cold Spring Harbor Laboratory Press) with acetate as a single carbon source, a total of three clones were grown. After isolation of the corresponding cosmids (Sambrook et al Molecular Cloning, A Laboratory Handbook, 1989, Cold Spring Harbor Laboratory Press), from these clones and renewed transformation in the *E. Coli* mutant DV21AO5, the resulting clones are only in a position to grow on the M9 medium with acetate as the single carbon source. This permits the surmise that the aceB gene from *C. glutamicum* is localized on the three cosmids.

Figure 1:
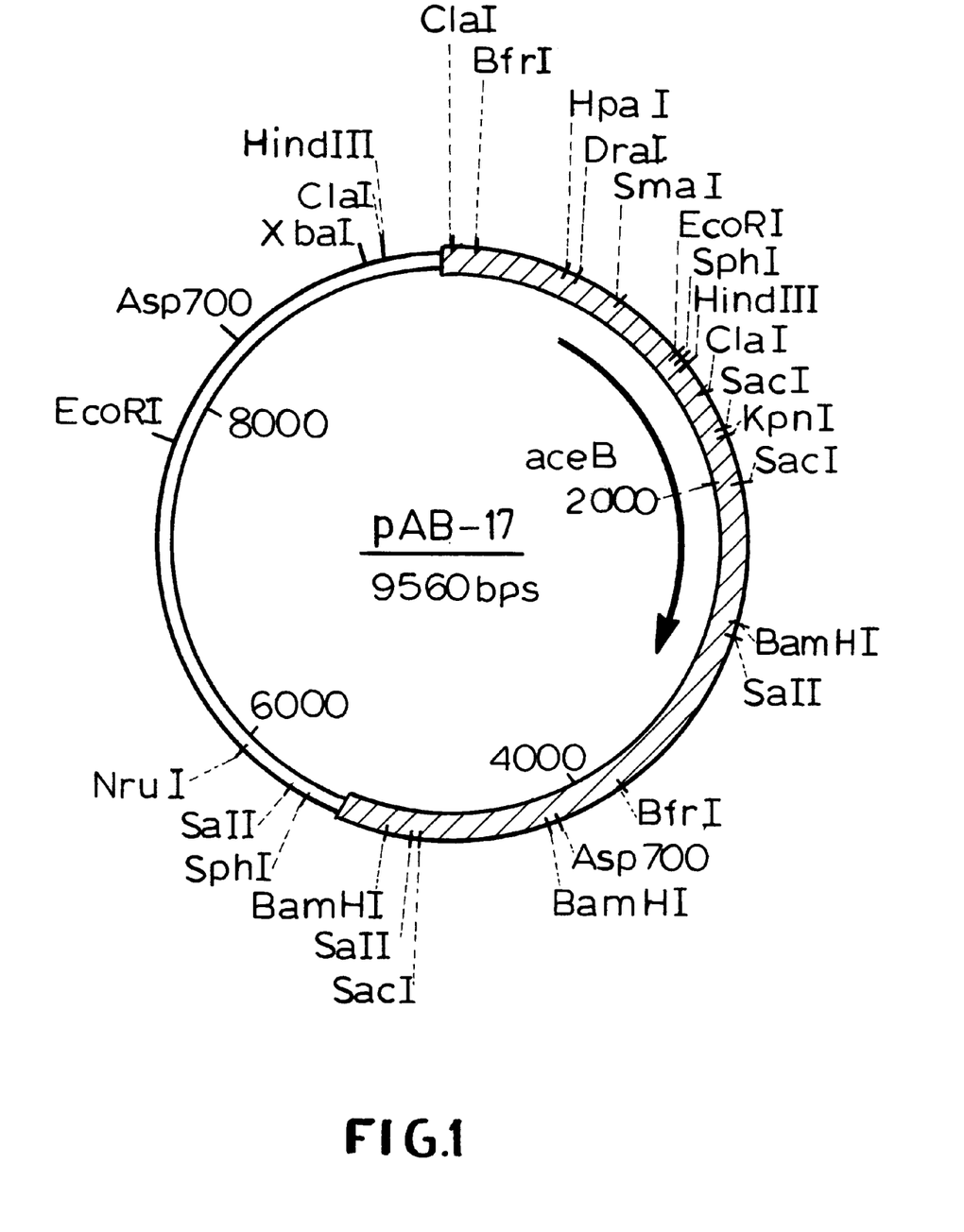
FIG. 1 is a restriction map of plasmid pAB-17.
Figure 2:
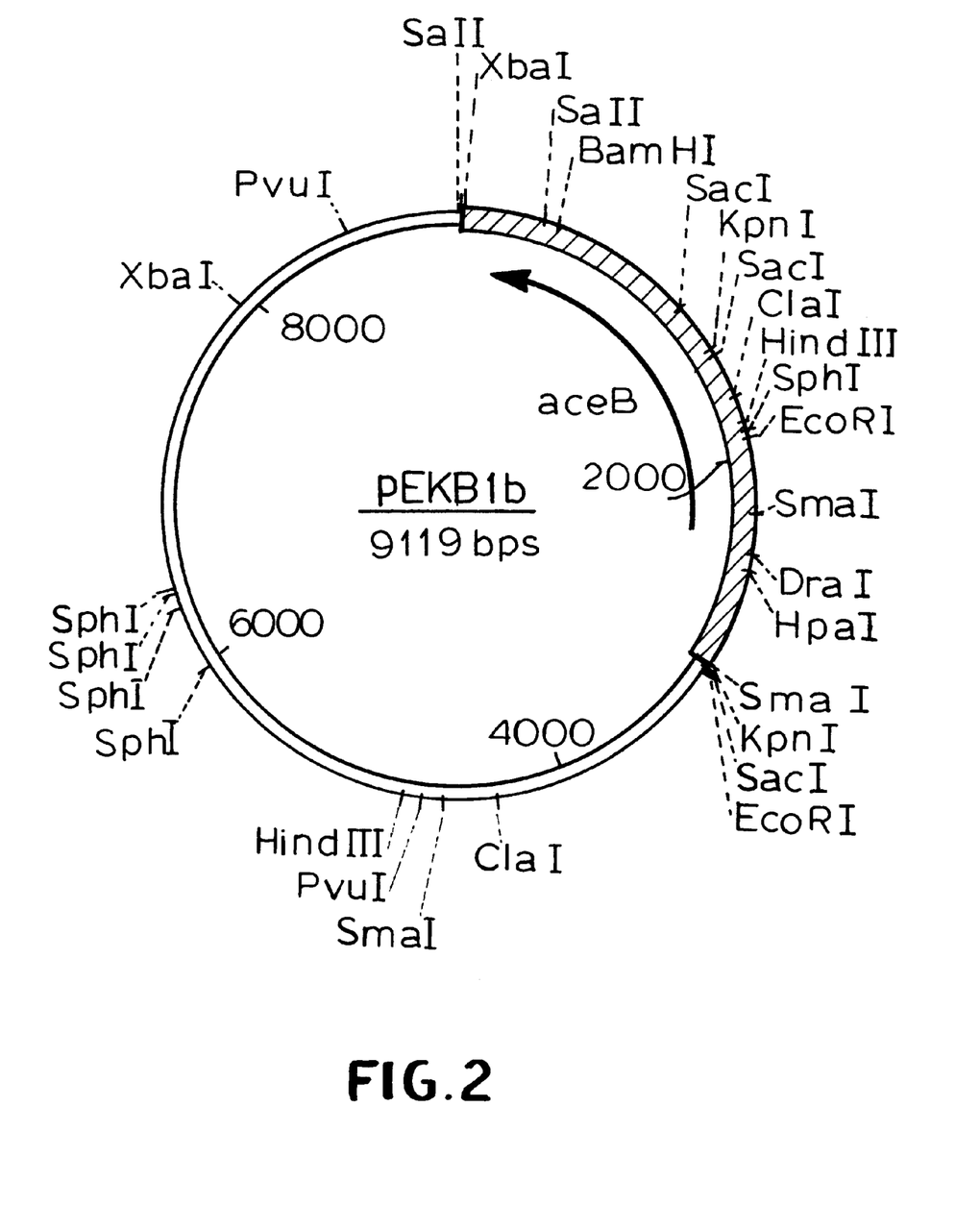
FIG. 2 is a restriction map of plasmid pEKB1b.
Figure 3:
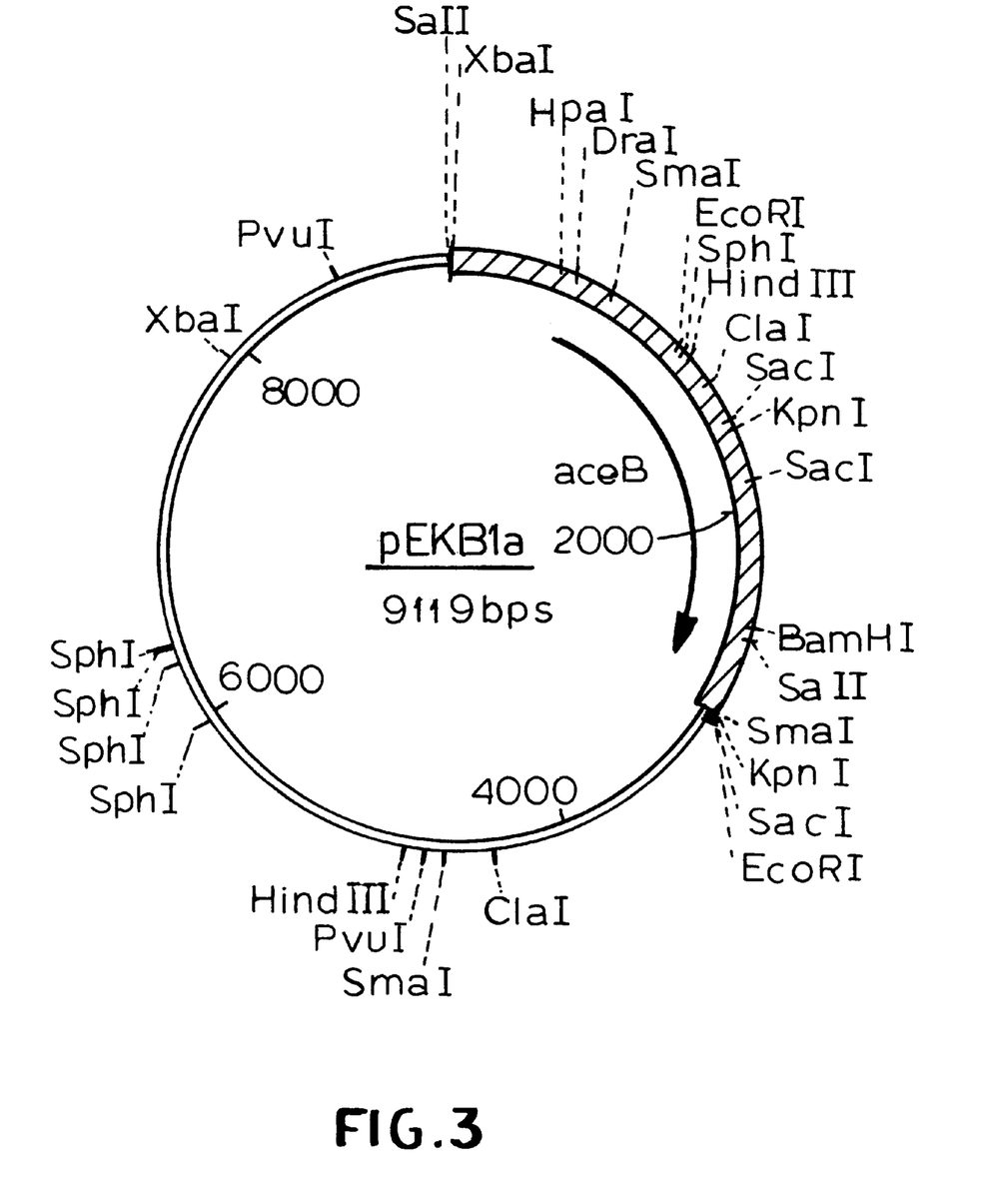

To limit the aceB gene from *C. glutamicum* to a smaller fragment, the three cosmids are partially digested with the restriction enzyme Sau3A and subjected to separation in an electric field on 0.8% agarose gel according to known methods (Sambrook et al Molecular Cloning, A Laboratory Handbook, 1989, Cold Spring Harbor Laboratory Press). Fragments in the size range of 3.0 kb to 6.0 kb are isolated from the gel by electroelution (Sambrook et al Molecular Cloning, A Laboratory Handbook, 1989, Cold Spring Harbor Laboratory Press) and ligated in the BamHI cleavage site of the vector pHCYC184 (Chang and Cohen, Journal of Bacteriologicals (1978) 1141–1156). With the ligation composition, *E. coli* DV21AO5 is transformed and the resulting transformant is investigated anew as to its ability to grow on acetate as a single carbon source. In this manner, nine clones are isolated whose plasmids enable the mutant DV21AO5 to grow on acetate. From the respective recombinant strains, the corresponding plasmids are isolated and subjected to restriction mapping. The restriction map of one of the plasmids pAB-17 is illustrated in FIG. 1. From this plasmid by known procedures, the DNS fragment coding for the MSY is isolated by BfrI-PvuI restriction as a 3 kb fragment and ligated in the *C. glutamicum/E. coli* swing vector PEKO (Eikmanns et al, Gene 102 (1991) 93–98). In dependence upon the orientation of the insert in the vector, the newly constructed plasmid is designated as peKB1a or pEKB1b. The restriction maps of both plasmids are presented in FIG. 2, and FIG. 3.

3. Analysis of the Nucleotide Sequence of the MSY Structure Gene and Bordering Regions.

For the sequencing, two overlapping partial fragments on 1.6 kb BfrI-KpnI and a 1.8 kb SphI-PvuI fragments are isolated from the plasmid paB-17 with known methods. The overhanging ends of both fragments are filled to smooth ends with Klenow-polymerase (Sambrook et al Molecular Cloning, A Laboratory Handbook, 1989, Cold Spring Harbor Laboratory Press) and ligated at suitable cut locations of the plasmid pUC18 (Vieira and Messing, Gene 19 (1982) 259–268). The so generated plasmid is used according to the method of Henikoff (Gene 28 (1984) 351–359) to produce deletion constructs which are then sequenced by the chain breakage sequencing method (Sanger et al., Procedures of the National Academy of Science 74 (1977) 5463–5467). The thus-obtained total sequence of the 3 kb BfrI-PvuI fragment is shown in Table 2. Apart from this, Table 2 shows the protein sequence which is derived from the aceB gene for an MSY from *C. glutamicum*, which ahead of the gene has ribosome binding sites and behind the gene has a termination structure for the transcription.

4. NOY Activity of *C. glutaxicum* Strains which Carry the MSY Gene on Plasaids.

By electroporation (Liebl et al, FEMS Microbiological Letters 65 (1989) 299–304), the plasmids pEKB1a and pEKB1b are inserted in *C. glutamicum* and the resulting strains are designated WT(pEKB1a) and WT(pEKB1b). By known methods the newly constructed *C. glutamicum* strains are cultured on CgC minimal medium with glucose, glucose/acetate or acetate as carbon sources up to $OD_{600}$ of 8 to 10, raw extracts are produced and the specific NSY activities are illustrated in Table 3.

The *C. glutamicum* strains WT(pEKB1a) and WT(pEKB1b) show significantly higher activities on all three carbon sources respectively than the *C. glutamicum* wild type WT(pEKO) which contains the starting vector pEKO. These results show a functional dependency of the activity upon the 3 kb BfrI-PvuI fragment from an aceB gene of *C. glutamicum*. After growth of the *C. glutamicum* strains WT(pEKB1a) and WT(pEKB1b) on CgC-glucose/acetate, their MSY activities are about eight times higher than with growth of these strains on glucose. With growth of both strains on CgC minimal medium with acetate as a single carbon source, the MSY activity is 16 to 18 times higher than with growth upon CgC glucose. These results underscore that the isolated fragment contains all of the structures of the aceB gene necessary for expression and regulation, i.e. the promoter and regulatory sequence. These structures lie ahead of the aceB gene.

Since the cloned fragment ahead of the characteristic aceB structure gene has 584 bp (Table 2) the structures for expression and regulation must be localized in this DNS region.

5. Investigation of the Regulation and Expression of the aceB Gene of *C. glutamicum*.

Figure 4:
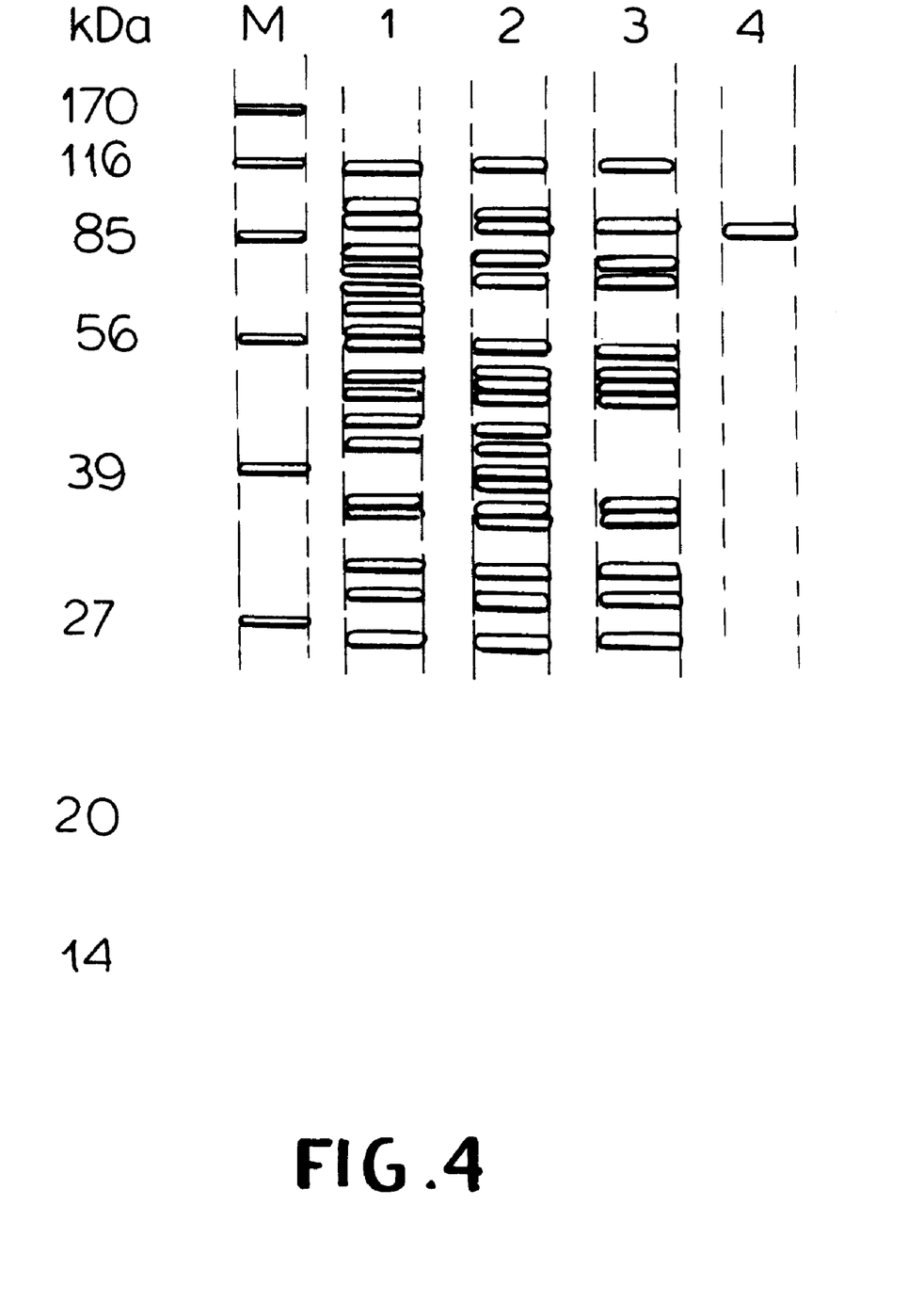

In order to ascertain that the observed regulation of MSY is a regulation on the genetic level and not a regulation of the enzyme itself (e.g. by inhibition, activation or covalent modification) raw extracts of the *C. glutamicum* WT (pEKB1a) cells grown on CgC minimal medium with glucose and *C. glutamicum* WT (pEKB1a) cells grown on CgC minimal medium with acetate are investigated with respect to their protein patterns. For this purpose, the mentioned strains are grown by known methods on the corresponding media, raw extracts are produced and these are separated by the method of Laemmli (Nature 227 (1970) 680–685) under denaturing conditions and are separated on 12.5% polyacrylamide gel (FIG. 4) for localization of the MSY-protein bands in the raw extract, the MSY from *C. glutamicum* is purified to homogeneity (see Appendix 1) and parallel to the raw extracts, are subjected to an electrophoresis under denaturing conditions (FIG. 4). After growth of *C. glutamicum* WT on CgC acetate, one notes at the level of the MSY, a clearly more intensive protein band than after growth of this strain on CgC acetate of very intensive MSY protein band. From the intensity of these bands one can conclude that the MSY in these strains makes up about 20% of the total cell protein. The results indicate that the structures necessary for the expression and regulation of aceB, under induced conditions give rise to a new synthesis of larger quantities of proteins. In addition, the results are clear that the observed increase in the MSY activity after growth on acetate is associated with the new synthesis of the MSY protein.

6. Test of the DNS Region Lying Ahead of the aceB Gene with Respect to Functionality in an Independent System.

The DNS region ahead of the aceB gene was isolated by known methods as the 574 bp BfrI-DraI fragment, the overhanging ends are filled with clean-out polymerization to smooth ends and ligated into the SalI cuts of the vector pEK-plCm (Eikmanns et al, Gene 102 (1991) 93–98). This plasmid carries behind the insertion side the chloramphenicol-acetyltransferase gene (cat) but without a respective promoter, i.e. the cat gene in *C. glutamicum* cannot be read from plasmid pEKp1Cm. After the ligation of the BfrI-DraI fragment in the vector pEKp1Cm it was determined by sequencing by known methods that the orientation of the BfrI-DraI fragment ahead of the cat gene corresponded to that ahead of the aceB gene. The corresponding plasmid was designated aspIWI. After introducing the plasmid pIWI in *C. glutamicum* by known methods, the activity of chloramphenicol-acetyltransferase (CAT) was determined in this strain after growth on CgC glucose, CgC glucose/acetate or CgC acetate. The strains to be invigorated were cultivated by known methods to an $OD_{600}$ of 8 to 10, raw extracts were produced and in these specific CAT activity was determined by the method of Shaw (Method of Enzymology 43 (1975) 737–755). The test contained in a final volume of 1.0 ml 100 mM Tris/HCl pH 7.8, 1 mM acetyl-coenzymeA, 1 mM of 5.5 dithiobis-(2-nitrobenzoic acid) and raw extract and was saturated with 2.5 mM chloramphenicol. The composition was incubated at 30° C. Over a period of 2 minutes the extinction increase at 412 nm was determined. The protein content of the raw extract was determined with the aid of the Biuret method (Bradford, Analogical Biochemistry 72 (1976) 248–254). The obtained CAT activities are given in Table 4. While CAT activity was found in the *C. glutamicum* WT under any of the test conditions, the recombinant strain *C. glutamicum* WT(pIWI) showed CAT activity with all carbon sources. However, the CAT activity after growth on CgC cellulose show about 20 times less than after growth on CgC glucose/acetate and 50 times smaller than after growth on CgC acetate. These results indicated that the isolated 574 bp BfrI-DraI fragment of the regulated gene expression promoted the presence of foreign genes. An induction of the foreign genes occurs with acetate, just as in the presence of sugar.

Appendix I

Purification of MSY from *C. glutamicum*.

For purification of MSY from C. glutamicum, 60 ml of a culture grown in CgC acetate medium to $OD_{600}$ 8 to 10 was used. The cells were washed twice with 20 ml 50 mM of morpholinoethansulfonic acid (MES)/NaOH pH 6.0 and resuspended in 1 ml of the same buffer after addition of 5U/ml Dnase, 15 µg/mg Rnase and 100 µm phenylmethylsulfonyl-fluoride, breakdown and removal of cell detritus is effected in accordance with already known methods. All purification steps are carried out at 40° C. The sole extract is diluted with 50 mM MES/NaOH pH 6 to 10 ml. After 2 hours of ultracentrifugation at 183,000×g the supernatant is chromatified on a FPLC apparatus with HR5/5 monoQ anion exchange column (Pharmacia LKB, Freiburg, Germany). During the first chromatographic purification the MSY is eluted 0.1 M to 0.4 M NaCl gradient in 50 mM MES/NaOH pH 6. For the second chromatography, the buffer is changed for the partially purified MSY by ultrafiltration from 50 mM MES/NaOH pH 6 to 50 mM Tris/HCl pH 8. During the second chromatographic purification the MSY is eluted with an 0.2 M to 0.5 M gradient in 50 mM Tris/HCl pH 8. During both chromatographic separations, a flow rate of 1 ml/min is maintained. The flushing of both separations is concluded in 1 ml/fractions and tested for MSY activity. The fractions containing the activity were combined.

TABLE 1

Activity of malate-synthase (MSY) in raw extracts of *Corynebacterium glutamicum* after growth on various carbon sources.

| Medium | Specific MSY-Activity (U/mg Protein) |
| --- | --- |
| 2xtY-complete medium | 0.030 |
| 2xTY-complete medium + 1% Acetate | 0.840 |
| CgC-minimum medium (MM) + 1% Glucose | 0.040 |
| CgC-MM + 1% Acetate | 2.212 |
| CgC-MM + 1% Pyruvate | 0.192 |
| CgC-MM + 1% Lactate | 0.173 |
| CgC-MM + 1% Citrate | 0.038 |
| CgC-MM + 1% Succinate | 0.045 |
| CgC-MM + 1% Fumarate | 0.034 |
| CgC-MM + 1% Glutamate | 0.041 |
| CgC-MM + 1% Acetate + 1% Glucose | 0.970 |
| CgC-MM + 1% Acetate + 1% Pyruvate | 0.730 |
| CgC-MM + 1% Acetate + 1% Lactate | 0.860 |
| CgC-MM + 1% Acetate + 1% Citrate | 0.500 |
| CgC-MM + 1% Acetate + 1% Succinate | 0.920 |
| CgC-MM + 1% Acetate + 1% Fumarate | 0.910 |
| CgC-MM + 1% Acetate + 1% Glutamate | 1.330 |

TABLE 2

```
   1 CTTAAGTGCTGATTCGCAATGGGCGGTGCCGACCACAAAGTATGAGCTAATGCACTGTCACTGTTTCGACGTGATGTGCATCGGTTTGCG

91 TGGTGGCGTGGTTCACACATTGCTCCATCGGGCATTGGTGCGTCAATCGGTTTGGGTTTTTAAGTTTTGTGCGGGGGTGGTCACCCCTGT

181 TGTGAAGTTTGCAAAGTTCTGGCTTCGCAGAAAAAGTGGGCGGGGGAGTTGCTAGTACGGATGTACTGGGCAAATGCTCTGAAATGGGAA

271 AATGCAGGCACCGCAACGTTCCGTAGGTTTCGAAGGTGTGACCTAGATAAAAGTCGGGGTTAGGCGGGGGTAATGACTTAGTAAAGTTCG

361 CAAACCCCTTTTGCTGGTGACGGTGATCACTTAGTCTGATCACATCGCCAAACACGATAAGGGTTGAAATCGAAAGAAGAGTGGCACCTA

451 GATTCCAGAGGTAGTCAGAGTGCTTTTCTTAAAAGAGTTTTCACAACCGTTAACGCGTAGCCAAACAAGAAGGATTCGCATTCTTCTGGT

541 TTAGGCACAGGTCATCTAAAACCCATGCTTTAAAAGGAGCCTTCAATGACTGAACAGGAACTGTTGTCTGCTCAGACTGCCGACAACGCT
                                   RBS           M  T  E  Q  E  L  L  S  A  Q  T  A  D  N  A

631 GGAACTGACAGCACCGAACGCGTTGACGCGGGCGGAATGCAGGTTGCAAAAGTTCTCTACGACTTTGTAACCGAAGCGGTACTCCCTCGC
      G  T  D  S  T  E  R  V  D  A  G  G  M  Q  V  A  K  V  L  Y  D  F  V  T  E  A  V  L  P  R

721 GTGGGTGTGGATGCGGAAAAGTTCTGGTCCGGATTCGCCGCCATCGCCCGGGACCTCACCCCACGCAACCGCGAGCTGCTTGCTCGCCGC
      V  G  V  D  A  E  K  F  W  S  G  F  A  A  I  A  R  D  L  T  P  R  N  R  E  L  L  A  R  R

811 GATGAACTGCAGATGCTTATCGACGACTACCACCGCAACAACTCCGGCACCATCGACCAAGAGGCGTACGAGGATTTCCTCAAAGAAATC
      D  E  L  Q  M  L  I  D  D  Y  H  R  N  N  S  G  T  I  D  Q  E  Q  Y  E  D  F  L  K  E  I

901 GGATACTTGGTTGAGGAGCCAGAAGCTGCAGAAATCCGTACCCAAAACGTCGATACGGAAATCTCCAGCACCGCAGGACCTCAGCTGGTT
       G  Y  L  V  E  E  P  E  A  A  E  I  R  T  Q  N  V  D  T  E  I  S  S  T  A  G  P  Q  L  V

991 GTTCCAATTCTGAACGCACGCTTCGCGCTGAACGCTGCCAATGCTCGCTGGGGTTCCCTCTACGATGCGTTGTACGGCACCAACGCCATC
      V  P  I  L  N  A  R  F  A  L  N  A  A  N  A  R  W  G  S  L  Y  D  A  L  Y  G  T  N  A  I

1081 CCAGAAACTGATGGCGCTGAAAAGGGCAAGGAGTACAACCCGGTCCGCGGCCAGAAGGTCATCGAGTGGGGTCGTGAATTCCTCGACAGC
      P  E  T  D  G  A  E  K  G  K  E  Y  N  P  V  R  G  Q  K  V  I  E  W  G  R  E  F  L  D  S

1171 GTTGTCCCACTGGACGGTGCTTCGCATGCCGATGTTGAGAAGTACAACATCACCGATGGAAAGCTTGCAGCCCACATTGGAGATAGCGTC
      V  V  P  L  D  G  A  S  H  A  D  V  E  K  Y  N  I  T  D  G  K  L  A  A  H  I  G  D  S  V

1261 TACCGACTGAAAAACCGTGAATCCTACCGTGGCTTCACCGGCAACTTCCTTGATCCAGAAGCAATCCTGCTGGAAACCAACGGCCTGCAC
      Y  R  L  K  N  R  E  S  Y  R  G  F  T  G  N  F  L  D  P  E  A  I  L  L  E  T  N  G  L  H

1351 ATCGAGCTGCAGATCGATCCTGTCCACCCAATCGGCAAGGCAGACAAGACTGGTCTCAAAGACATCGTTTTGGAATCTGCGATCACCACG
      I  E  L  Q  I  D  P  V  H  P  I  G  K  A  D  K  T  G  L  K  D  I  V  L  E  S  A  I  T  T

1441 ATCATGGACTTCGAAGACTCCGTTGCAGCTGTTGATGCTGAAGACAAGACCTTAGGTTACTCTAACTGGTTCGGACTCAACACCGGCGAA
      I  M  D  F  E  D  S  V  A  A  V  D  A  E  D  K  T  L  G  Y  S  N  W  F  G  L  N  T  G  E

1531 CTGAAAGAAGAGATGTCCAAGAACGGACGCATCTTCACCCGTGAGCTCAACAAGGACCGCGTCTACATTGGCCGCAATGGTACCGAGCTG
      L  K  E  E  M  S  K  N  G  R  I  F  T  R  E  L  N  K  D  R  V  Y  I  G  R  N  G  T  E  L

1621 GTTCTGCACGGTCGTTCCCTGCTGTTCGTCCGCAACGTTGGTCACCTCATGCAAAACCCATCCATCTTGATTGATGGCGAGGAGATCTTC
      V  L  H  G  R  S  L  L  F  V  R  N  V  G  H  L  M  Q  N  P  S  I  L  I  D  G  E  E  I  F

1711 GAAGGCATCATGGATGCTGTCTTGACCACTGTTTGTGCCATCCCAGGAATTGCTCCGCAGAACAAGATGCGCAATTCCCGCAAGGGCTCC
      E  G  I  M  D  A  V  L  T  T  V  C  A  I  P  G  I  A  P  Q  N  K  M  R  N  S  R  K  G  S
```

TABLE 2-continued

```
1801 ATCTACATCGTGAAGCCTAAGCAGCACGGCCCTGAAGAAGTCGCGTTCACCAACGAGCTCTTCGGCCGCGTTGAGGATCTGCTTGATCTG
        I   Y   I   V   K   P   K   Q   H   G   P   E   E   V   A   F   T   N   E   L   F   G   R   V   E   D   L   L   D   L
1891 CCACGCCACACCTTGAAGGTTGGTGTTATGGATGAGGAGCGTCGCACGTCCGTGAACCTGGATGCCAGCATCATGGAAGTTGCTGACCGC
        P   R   H   T   L   K   V   G   V   M   D   E   E   R   R   T   S   V   N   L   D   A   S   I   M   E   V   A   D   R
1981 TTGGCATTCATCAACACTGGCTTCCTGGACCGCACCGGCGATGAAATCCACACCTCCATGGAAGCAGGCGCCATGGTGCGCAAGGCTGAT
        L   A   F   I   N   T   G   F   L   D   R   T   G   D   E   I   H   T   S   M   E   A   G   A   M   V   R   K   A   D
2071 ATGCAGACCGCACCGTGGAAGCAGGCCTACGAGAACAACAACGTTGATGCAGGTATTCAGCGTGGTCTTCCTGGCAAGGCTCAGATCGGT
        M   Q   T   A   P   W   K   Q   A   Y   E   N   N   N   V   D   A   G   I   Q   R   G   L   P   G   K   A   Q   I   G
2161 AAGGGCATGTGGGCGATGACTGAACTCATGGCAGAAATGCTGGAGAAGAAGATCGGCCAGCCACGCGAAGGCGCCAACACTGCATGGGTT
        K   G   M   W   A   M   T   E   L   M   A   E   M   L   E   K   K   I   G   Q   P   R   E   G   A   N   T   A   W   V
2251 CCTTCACCAACTGGTGCGACGCTGCACGCAACGCACTACCACTTGGTTGATGTGTTCAAGGTTCAAGACGAACTGCGTGCTGCCGGCCGC
        P   S   P   T   G   A   T   L   H   A   T   H   Y   H   L   V   D   V   F   K   V   Q   D   E   L   R   A   A   G   R
2341 CGCGACAGCCTGCGCAACATTCTCACCATTCCAACCGCACCAAACACCAATTGGTCTGAGGAAGAGAAGAAGGAAGAGATGGACAACAAC
        R   D   S   L   R   N   I   L   T   I   P   T   A   P   N   T   N   W   S   E   E   E   K   K   E   E   M   D   N   N
2431 TGCCAGTCCATCCTCGGATACGTTGTGCGCTGGGTTGAGCACGGTGTTGGTTGCTCCAAGGTTCCAGACATCCATGACATCGACCTCATG
        C   Q   S   I   L   G   Y   V   V   R   W   V   E   H   G   V   G   C   S   K   V   P   D   I   H   D   I   D   L   M
2521 GAAGACCGCGCAACGCTGCGTATTTCCTCGCAGATGCTGGCCAACTGGATCCGCCATGATGTTGTCTCGAAGGAGCAGGTCTTGGAGTCA
        E   D   R   A   T   L   R   I   S   S   Q   M   L   A   N   W   I   R   H   D   V   V   S   K   E   Q   V   L   E   S
2611 CTGGAACGAATGGCAGTGGTCGTCGACAAGCAAAATGCGGGCGACGAGGCCTACCGCGATATGGCGCCGAACTACGACGCCTCCCTCGCC
        L   E   R   M   A   V   V   V   D   K   Q   N   A   G   D   E   A   Y   R   D   M   A   P   N   Y   D   A   S   L   A
2701 TTCCAGGCGGCTAAGGACTTGATTTTCGAAGGCACCAAGTCCCCATCGGGCTACACCGAGCCCATCTTGCACGCACGCCGCCGCGAGTTC
        F   Q   A   A   K   D   L   I   F   E   G   T   K   S   P   S   G   Y   T   E   P   I   L   H   A   R   R   R   E   F
2791 AAAGCAAAAAACTAAGCACGCTTTTCGACGCTTACCTGCATCCCAACGGTGACTGACTGCCCCGGAGCCACCCTCACTCCTTTTTGGTCA
        K   A   K   N
2881 GCACCCAAAAGCGCCGGTTCAACACACACAAAGTCGCGCCATTCACCTTCGCCAATATCGGCCACGGTGGAGGCGCGACTTTCGCCTGGA
                                      ──────────────────────→       ←──────────────────────
2971 TTCCACACCACAGTGGAATCATGACCATCGCCCTCAATGGTGATGATGCGATCG
```

| TABLE 3 |
|---|
| Specific Activity of Malate Synthase (MSY) in Raw Extracts of the *C. glutamicum* Wild Types and the Recombinant *C. glutamicum* with the Plasmids pEKO, pEKB1a and pEKB1b after Growth on CgC-Minimum Medium with Glucose, Glucose/Acetate or Acetate as Carbon Sources. |

| C. glutamicum-Strain | Specific CgC-Glucose | MSY-Activity CgC-Glucose/Acetate | (U/mg Protein) CgC-Acetate |
|---|---|---|---|
| WT | 0.040 | 0.970 | 2.11 |
| WT(pEKO) | 0.038 | 0.954 | 2.23 |
| WT(pEKB1a) | 0.350 | 3.120 | 6.22 |
| WT(pEKB1b) | 0.374 | 3.240 | 6.08 |

| TABLE 4 |
|---|
| Specific Activity of Chloramphenicol-Acetyltransferase (CAT) in Raw Extracts of *C. glutamicum* Wild Types (WT) and the Recombinant *C. glutamicum* strains (WT) (pIWI) after growth on CgC-Minimum Medium with Glucose, Glucose/Acetate or Acetate as Carbon Sources. |

| C. glutamicum- | Specific CgC-Glucose | CAT-Activity CgC-Glucose/Acetate | (U/mg Protein)Strain CgC-Acetate |
|---|---|---|---|
| WT | 0.001 | 0.001 | 0.001 |
| WT(pIWI) | 0.026 | 0.620 | 1.320 |

We claim:

1. An isolated recombinant polynucleotide comprising the nucleic acid sequence as given in SEQ ID NO: 3.

2. The isolated recombinant polynucleotide defined in claim 1 further comprising a structural gene located downstream of said isolated polynucleotide.

3. A vector containing an isolated polynucleotide comprising the nucleic acid sequence as given in SEQ ID NO: 3.

4. The vector containing an isolated polynucleotide defined in claim 3 further comprising a structural gene located downstream of said isolated polynucleotide.

5. A transformed Coryneform cell containing the vector defined in claim 3.

6. A transformed microorganism containing in replicatable form the isolated polynucleotide comprising the nucleic acid sequence as given in SEQ ID NO: 3.

7. The transformed microorganism defined in claim 6 wherein the recombinant microorganism is a transformed Coryneform cell.

8. A method for synthesizing a protein by expressing a structural gene coding for said protein, which comprises the following steps:

(a) transforming a microorganism with a vector containing an isolated polynucleotide comprising the nucleic acid sequence as given in SEQ ID NO: 3 and downstream thereof a structural gene coding for said protein;

(b) culturing said microorganism in a medium to which an inductor has been added to express said structural gene; and (c) recovering the protein expressed by the structural gene.

9. The method defined in claim 8 wherein according to step (b) the inductor is lactate, pyruvate or acetate.

10. The method defined in claim 8 wherein according to step (a) the microorganism is a coryneform bacterium.

* * * * *